(12) United States Patent
Weipert

(10) Patent No.: US 6,500,981 B1
(45) Date of Patent: Dec. 31, 2002

(54) HYDROXY AND SULFONIC ACID SUBSTITUTED ALKENES AND SALTS

(75) Inventor: Paul David Weipert, High Point, NC (US)

(73) Assignee: Ethox Chemicals LLC, Greenville, SC (US)

( * ) Notice: Subject to any disclaimer, the term of this patent is extended or adjusted under 35 U.S.C. 154(b) by 143 days.

(21) Appl. No.: 09/631,688

(22) Filed: Aug. 2, 2000

(51) Int. Cl.$^7$ ............................................. C07C 309/20
(52) U.S. Cl. ....................................................... 562/108
(58) Field of Search ................................. 562/108, 111

(56) References Cited

U.S. PATENT DOCUMENTS 5,221,443 A * 6/1993 Voss

* cited by examiner

Primary Examiner—Christopher Henderson
(74) Attorney, Agent, or Firm—Isaac A. Angres

(57) ABSTRACT

The present invention provides water soluble ethylenically unsaturated monomers selected from the group consisting of formula I and II

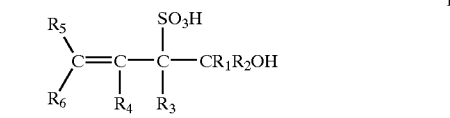

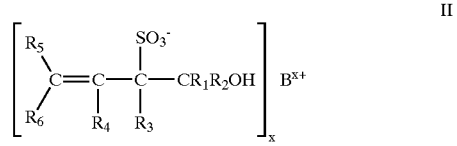

wherein $R_1$, $R_2$, $R_3$, $R_4$, $R_5$, and $R_6$ are independently selected from the group consisting of hydrogen, and $C_1$–$C_5$ primary, secondary or tertiary lower alkyl group; B is a monovalent or multivalent metal selected from the group consisting of alkali metals, alkaline earth metals and transition metals; and x represents the stoichiometric valence requirement of the molecule. The invention also provides polymers and emulsions derived from the above monomers.

5 Claims, No Drawings

HYDROXY AND SULFONIC ACID SUBSTITUTED ALKENES AND SALTS

FIELD OF INVENTION

This invention relates to new ethylenically unsaturated monomers derived from the reaction of epoxy substituted alkenes and sodium bisulfite. The instant invention is also directed to polymers derived from the above ethylenically unsaturated monomers. This invention also relates to a new ethylenically unsaturated monomer derived from the reaction of 3,4-epoxy-1-butene and sodium bisulfite. The invention is also directed to a new compound known as 4-hydroxy-3-sulfonic acid-1-butene and metallic salts thereof. This invention further relates to polymers and copolymers derived from 4-hydroxy-3-sulfonic acid-1-butene, metallic salts thereof and ammonium and amine salts thereof. The present invention is also directed to self-dispersing polymers and copolymers containing the novel ethylenically unsaturated monomer of the instant invention.

This invention also relates to polymerizable sulfonic acid derivatives, to processes for their production and to their use as emulsifiers for aqueous emulsions. The invention is further directed to polymers synthesized from the emulsifiers and other monomers.

The present invention also relates to a method of producing an aqueous polymer emulsion having excellent stability. More specifically, the present invention is also intended for producing an aqueous emulsion containing substantially no emulsifier and relates to a method of producing an aqueous polymer emulsion remarkably elevated in chemical stability by copolymerizing a specific amount of a particular vinyl monomer containing hydroxy and sulfonate moieties as an indispensable copolymerization component.

The present invention also relates to polymeric compositions specially acrylic resin compositions having excellent permanent antistatic properties and a method for the production thereof.

The instant invention also relates to novel ampholyte polymers, polymer compositions and methods for using such polymers and compositions in personal care applications. In general terms, the polymers and polymer compositions of the present invention are believed to be useful in the treatment of keratin-containing substrates. Keratin substrates include, but are not limited to, animal and human hair, skin and nails.

More particularly, the instant invention relates to polymer compositions and methods for treating keratin in which a cosmetically acceptable medium is used which contains at least about 0.01% by weight of an ampholyte polymer comprising acrylamidopropyltrimethyl ammonium chloride or methacrylamido-propyltrimethyl ammonium chloride; acrylic acid, methacrylic acid, 4-hydroxy-3-sulfonic acid-1-butene sodium salt and, optionally, an alkyl (meth)acrylate. Preferably, the cosmetically acceptable medium is a hair care product such as a shampoo, conditioner, styling product or rinse, or a skin care product such as a cleaner, lotion or cream.

BACKGROUND OF THE INVENTION

In order to maintain the stability of aqueous polymer emulsions, it has been generally the practice heretofore in producing such emulsions to add a low molecular weight emulsifier upon polymerization or to compound a low molecular weight emulsifier or dispersant after polymerization. In recent years, there is an increasing demand in using aqueous polymer emulsions for paints, cement or mortar mixing, adhesives, textile treatment and paper processing. For such applications, the emulsion in intact form is usually used and not the polymer itself removed from the emulsion. Accordingly, when the emulsion contains an emulsifier or dispersant, foaming of the emulsion will occur on account of the emulsifier, etc. contained, and this makes it handling upon processing extremely difficult. Of course, the addition of a defoaming agent is attempted to prevent foaming, but when such an emulsion containing a defoaming agent is used for the above-mentioned purposes such as paint or cement, the mechanical strength or moisture-proofing of the film or shaped product will be seriously lowered by the secondary action of the emulsifier or defoaming agent, and this will constitute a great hindrance in practical use.

In order to obviate the defects attendant on such emulsifier-containing emulsions, aqueous emulsions free from low molecular weight emulsifiers have been noted in recent years, and many research investigations are being made of such emulsifier-free aqueous polymer emulsions or methods for producing the same.

Emulsifier-free aqueous polymer emulsions have various excellent features in comparison with the conventional emulsifier-containing emulsions. But on the other side, they involve a defect such that they are remarkably low in chemical stability, particularly in the stability against electrolytes, in comparison with the usual emulsifier-containing emulsions, and easily precipitate or coagulate by the addition of a small amount of electrolytes. Such defects present various problems and pose difficulties in practical use for applications wherein large amounts of electrolytes and other substances are mixed, as in paints, cement or mortar mixing, adhesives, paper processing and textile treatment.

Furthermore, in the emulsion (suspension) polymerization of ethylenically unsaturated monomers, :one or more surfactants (or emulsifiers) are employed conventionally to emulsify the monomer reactant(s) and the resulting polymer product latex. Such surfactants do not become chemically bonded to the polymer product molecule by carbon to carbon bonding (as distinct from a physical mixture, being absorbed on the polymer product or the like). It has been suggested that the small amount of surfactant which remains in the polymer product latex may interfere with performance of products, e.g., coatings and adhesives, prepared from such latex. U.S. Pat. No. 3,941,857 reports that coatings prepared from vinyl chloride/olefin copolymers show inconsistent performance in hot water resistance and tend to be sensitive to water in that pitting or "blushing" (a whitening effect) may sporadically occur, particularly after exposure of the coating to boiling water for extended periods. Such a performance characteristic is detrimental to certain end uses for such copolymers, e.g., container and paper coatings, interior and exterior coatings, industrial coatings, automotive coatings and certain adhesives.

Various proposals have been made for avoiding the reported adverse effects of surfactant residues in emulsion polymerized polymers. U.S. Pat. No. 3,941,857 describes incorporating a small amount of an epoxy resin with a vinyl chloride/olefin copolymer resin before casting a film from the resin. U.S. Pat. No. 4,049,608 describes the use of esters of an alkenoic acid selected from the group consisting of cinnamic acid and alkenoic acids of from 4 to 18 carbon atoms with a hydroxyalkane sulfonic acid in the emulsion polymerization of vinyl and other ethylenically unsaturated monomers. These esters serve the dual function of emulsifier and co-monomer. U.S. Pat. No. 4,224,455 describes a class of ringed sulfonated half esters of maleic anhydride and alkoxylated alkyl arylols. These esters are reported to be anionic emulsifiers (surfactants) and reactive functional monomers that are copolymerizable under emulsion polymerization conditions. U.S. Pat. No. 4,337,185 describes use of a reactive polymeric surfactant which is a substantially linear synthetic water-soluble surfactant whose polymeric backbone is derived from the polymerization of one or more ethylenically unsaturated monomers and which polymeric surfactant has a number average molecular weight of from about 500 to about 40,000 and contains various functional groups.

Also it is well known that acrylic resins have excellent gloss, transparency weatherability, excellent mechanical properties, and processability, and hence, are widely used for the preparation of advertising displays, lighting fixtures, covers, nameplates, and various decorations. However, because of their static properties, the acrylic resin products are easily charged by rubbing, etc. and the surface thereof is adhered with dust or rubbish, which results in deterioration of the beautiful appearance and in warping of the pointer of an instrument panel. There have been proposed various methods for imparting antistatic properties to the chargeable acrylic resin products. Such methods are roughly classified as follows: (1) a method of adding surfactants or fatty acid esters of a polyvalent alcohol to the acrylic resin; (2) a method of coating a silicon compound etc. onto the surface of the acrylic resin formed products and (3) a method of chemically modifying the resin structure by polymerizing the resin with a monomer having a hydrophilic group.

As the first method wherein a surfactant etc. is added thereto, there are proposed a method of using higher fatty acid monoglycerides (Japanese Patent Publication (unexamined) No. 112949/1978), and a method of adding an alkyldiethanolamine derivative (Japanese Patent Publication No. 21023/1978). According to this method, however, the surfactants etc. do not chemically bind to the acrylic resins, and hence, when the products are washed with water or rubbed, the products easily lose their antistatic properties. Besides, when a large amount of surfactants etc. are added thereto, the mechanical properties of the resin are deteriorated, and further, the surfactants etc. are easily bled to the surface thereof, by which the surface becomes sticky. Accordingly, the products are more easily adhered with dust or rubbish, which results in deterioration of the appearance.

It is also disclosed in Japanese Patent Publication (unexamined) No. 109944/1975 that a sulfonyl group-containing compound, a polyoxyalkylene glycol and a phosphite compound are admixed to the acrylic resin in order to impart antistatic properties thereto. However, only benzenesulfonic acid and toluenesulfonic acid are exemplified as the sulfonyl group-containing compound in this disclosures, and such sulfonic acids do not chemically bind to the acrylic resin and further show inferior compatibility with the acrylic resin. Hence, this method deteriorates the peculiar characteristics of the acrylic resin, i.e. surface gloss and transparency.

As the second method wherein a silicon compound is coated on the surface of the product, there is proposed, for example, a method of coating a solution of a partial hydrolysate of ethyl silicate onto the surface of the product (Japanese Patent Publication No. 6533/1956). This surface coating method is, effective for obtaining excellent antistatic properties which are durable, and thus, this method is practically used in some utilities. However, this method requires the steps of coating the antistatic agent onto the products and drying thereof, and therefore, this method has a problem with cost. This method also has drawbacks in that the coating film is easily broken by impact or rubbing to lose the antistatic properties.

As the third method wherein the structure of the resin per se is chemically modified, there is proposed, for example, a method of copolymerizing an acrylic monomer with a polyalkylene glycol monomethacrylate in order to improve the antistatic properties (Japanese Patent Publication (unexamined) No. 139516/1981). According to this method, a nonionic monomer is chemically bound to the resin, and hence, the undesirable dissolving out of the monomer is prevented, but the effect is not significant. Moreover, when a large amount of the nonionic monomer is incorporated, the resin exhibits reduced mechanical properties and lower heat resistance and the characteristics of the acrylic resin are significantly deteriorated. There is no method which can be employed practically.

Among the sulfonate-containing monomers which are known to exhibit antistatic properties, monomers which are hardly dissolved in methyl methacrylate, for example, sodium allylsulfonate, sodium methallylsulfonate, sodium vinylsulfonate, sodium alkenyl-aromatic sulfonate, or sodium methacryloxyalkylsulfonate, are not effectively used for the acrylic resin, because of their low compatibility with the resin, which causes a significant decrease in the characteristics of the acrylic resin, such as transparency, surface gloss, and as such, the products cannot practically be used.

The present inventor has carried out extensive studies on an improved acrylic resin composition which has excellent permanent antistatic properties without deteriorating the peculiar appearance of the acrylic resin. As a result, it has been found that a copolymer of an acrylic monomer and a small amount of the monomers of the present invention can be incorporated in order to give more enhanced properties, and further that the desired composition can be prepared by copolymerizing an acrylic monomer or a partial polymerizate thereof with the monomers of the present invention.

It is also well known that the surface properties of keratin are of interest in cosmetic science, and there has been a long-standing desire to discover ingredients which will beneficially affect the topical and bulk condition of keratinous substrates, such as hair. For example, such ingredients must have adequate adherent properties, so that they are not only adsorbed initially, but are also retained on exposure to water. This property is referred to as "substantivity", i.e., the ability of a material to be adsorbed onto keratin and to resist removal by water rinse-off.

Hair is composed of keratin, a sulfur-containing fibrous protein. The isoelectric point of keratin, and more specifically of hair, is generally in the pH range of 3.2–4.0. Therefore, at the pH of a typical shampoo, hair carries a net negative charge. Consequently, cationic polymers have long been used as conditioners in shampoo formulations, or as a separate treatment, in order to improve the wet and dry combability of the hair. The substantivity of the cationic polymers for negatively charged hair along with film formation facilitates detangling during wet hair combing and a reduction in static flyaway during dry hair combing. Cationic polymers generally also impart softness and suppleness to hair.

When cationic polymers are added to shampoos (or to skin care products such as cleaning compositions) containing anionic surfactants, formation of highly surface active association complexes generally takes place, which imparts improved foam stability to the shampoo. Maximum surface activity and foam stability, or lather, are achieved at near stoichiometric ratios of anionic surfactant: cationic polymer, where the complex is least water soluble. Generally, cationic conditioners exhibit some incompatibility at these ratios. Compatibility gives a commercially more desirable clear formulation, while incompatibility leads to a haze or precipitation, which is aesthetically less desirable in some formulations.

Hair fixative properties such as curl retention are believed to be directly related to film forming properties of cationic polymers, as well as to molecular weight, with performance generally increasing with increasing molecular weight. However, the fixative properties conferred by cationic polymers generally tend to have a reciprocal relationship to other conditioning properties, i.e., good curl retention usually means that properties such as wet compatibility will suffer, and vice versa. Accordingly, there is a long felt need for polymers in the cosmetic field having hydroxy and sulfonate functionality such as the polymers described in the present invention.

The present invention provides a novel group of ethylenically unsaturated monomers containing hydroxy and sulfonate moieties that display surfactant activity, i.e., they function as surfactants (emulsifiers) in emulsion (suspension) polymerization processes. Moreover, they are copolymerizable with ethylenically unsaturated monomers, including vinyl monomers, of the type commonly employed in emulsion polymerization processes by virtue of the reactive double bond present in the compounds. In accordance with the present invention, there is provided a novel group of compounds having a hydrophobic portion containing ethylenic: unsaturation, and a hydrophilic portion containing a hydroxy group and a sulfonate group.

OBJECTS OF THE INVENTION

It is a first object of the present invention to provide novel polymerizable ethylenically unsaturated monomers having hydroxyl and sulfonate functionality.

It is another object of the instant invention to provide novel polymerizable ethylenically unsaturated monomers having hydroxyl and sulfonate functionality having properties as emulsifying agent and dispersing agents.

A further object of the invention is to provide a novel polymerizable emulsifying agents having hydroxyl and sulfonate moieties which are capable of preventing a discharge of an environmental pollutant such as emulsifying agent, water-soluble polymeric material, water-soluble oligomer or oil-soluble oligomer in an aqueous emulsion polymerization of α, β-ethylenically unsaturated monomer.

A still further object of the invention is to provide novel polymerizable emulsifying and dispersing agents which can give a polymer having improved properties such as transparency, heat stability, mechanical property, fastness to light, impact strength, heat flowability and processing property.

An additional object of the invention is to provide a novel process for emulsion-polymerizing α, β-ethylenically unsaturated monomer employing the specific polymerizable emulsifying agent.

Still further object of the invention is to provide an improved aqueous emulsion polymerization process for α, β-ethylenically unsaturated monomer which does not discharge an environmental pollutant such as emulsifying agent, water-soluble polymeric material, water-soluble oligomer or oil-soluble oligomer in a step such as filtration and washing of polymer.

An additional object of the present invention is a method of advantageously obtaining an emulsifier-free aqueous polymer emulsion having excellent chemical stability which has not been easily attained by the conventional emulsifier- or dispersant-free aqueous emulsions.

Another main object of the present invention is to provide an aqueous polymer emulsion having remarkably improved properties for use in paints, cement or mortar mixing, film formation, adhesives, textile treatment and paper processing.

Another object of the present invention is to provide an improvement in antistatic properties of polymeric resins derived from ethylenically unsaturated monomers, especially acrylic resin without deteriorating the peculiar characteristics of the acrylic resin, such as excellent appearance, surface gloss, mechanical properties, etc.

These and other objects of the invention will become apparent from the description hereinafter.

SUMMARY OF THE INVENTION

Briefly, the present invention is directed to water soluble ethylenically unsaturated monomers selected from the group consisting of formula I and II

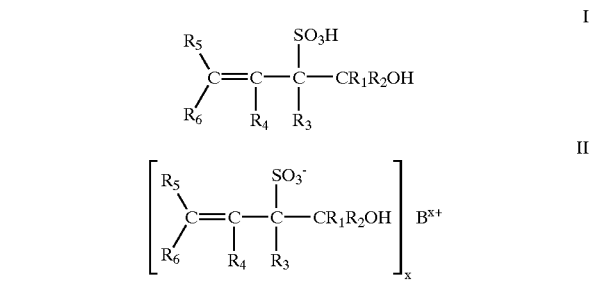

wherein $R_1$, $R_2$, $R_3$, $R_4$, $R_5$, and $R_6$ are independently selected from the group consisting of hydrogen, and $C_1$–$C_5$ primary, secondary or tertiary lower alkyl group; B is a monovalent or multivalent metal selected from the group consisting of alkali metals, alkaline earth metals and transition metals; and x represents the stoichiometric valence requirement of the molecule.

The invention is also directed to a polymer comprising at least one repeating unit of a compound corresponding to formula (I) or (II):

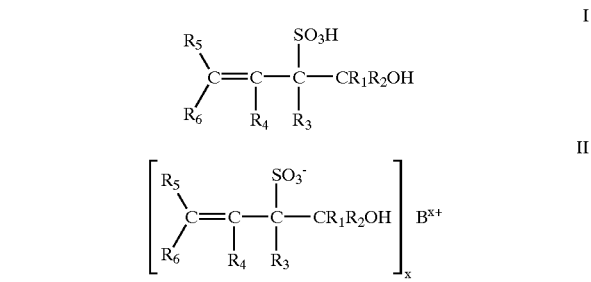

wherein $R_1$, $R_2$, $R_3$, $R_4$, $R_5$, and $R_6$ are independently selected from the group consisting of hydrogen, and $C_1$–$C_5$ primary, secondary or tertiary lower alkyl group; B is a monovalent or multivalent metal selected from the group consisting of alkali metals, alkaline earth metals and transition metals; and x represents the stoichiometric valence requirement of the molecule and the polymer contains at least one additioner monomer.

The instant invention also relates to a cosmetically acceptable medium containing from about 0.1 to about 20%, based on the weight of said medium, of the above polymer.

The invention is also directed to an article of manufacture comprising a substrate coated on at least one side with an interpolymer comprising:

(a) a monomer having the formula (I) or (II):

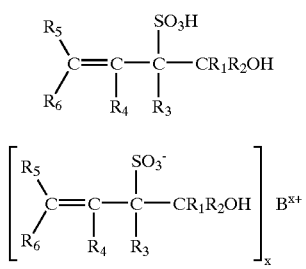

wherein $R_1$, $R_2$, $R_3$, $R_4$, $R_5$, and $R_6$ are independently selected from the group consisting of hydrogen, and $C_1$–$C_5$ primary, secondary or tertiary lower alkyl group; B is a monovalent or multivalent metal selected from the group consisting of alkali metals, alkaline earth metals and transition metals; and x represents the stoichiometric valence requirement of the molecule;

(b) optionally one monomer selected from the group consisting of esters of acrylic acid and methacrylic acid containing from 6 to 20 carbon atoms, alone, or with (c) optionally a monomer selected from the group consisting of alpha-olefins containing from 2 to 10 carbon atoms, vinyl esters of alkanoic acids containing from 3 to 10 carbon atoms, ethyl and methyl esters of acrylic and methacrylic acids, acrylonitrile, methacrylonitrile, styrene, vinyl toluene, and vinyl chloride, wherein the interpolymer has a weight average molecular weight in the range 10,000 to 1,000,000 and a glass transition temperature in the range of –15° to –75° C.

The invention is also directed to an ink comprising an aqueous medium, a water-insoluble colorant including a pigment, and a dispersant for dispersing said colorant in said aqueous medium, wherein said dispersant is a water-soluble polymer as described above. The inks which can form a recorded image have excellent fastness such as water resistance, light resistance, etc. and is also superior in storage stability and jetting stability.

The instant invention is further directed to a process for preparing acrylic polymers comprising aqueous-suspension polymerization carried out in the presence of 0.05–1% by weight, calculated on the suspension, of a stabilizer consisting of the polymer as described above.

The invention also features an ampholyte polymer comprising: (a) about 25 to about 75 mol % acrylamidopropyltrimethyl ammonium chloride or methacrylamidopropyltrimethyl ammonium chloride, alone or in combination; (b) about 25 to about 75 mol %-hydroxy-3-sulfonic acid-1-butene sodium salt, acrylic acid, methacrylic acid, alone or in combination; and (c) about 0.1 to about 20 mol % of a $C_1$–$C_{22}$ straight or branched chain alkyl acrylate or methacrylate.

The invention also relates to adhesive compositions as well as pressure sensitive adhesive formulations incorporating polymers derived from the monomers of the present invention.

DESCRIPTION OF THE PREFERRED EMBODIMENTS

In the first preferred embodiment, the present invention is directed to ethylenically unsaturated monomers corresponding to the following chemical structures I and II:

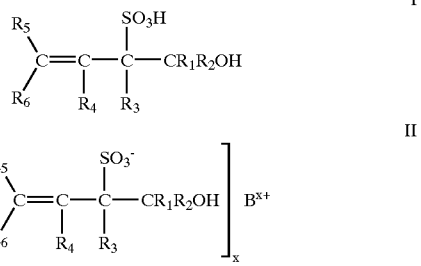

wherein $R_1$, $R_2$, $R_3$, $R_4$, $R_5$ and $R_6$ are independently selected from the group consisting of hydrogen, and $C_1$–$C_5$ primary, secondary or tertiary lower alkyl group; B is a monovalent or multivalent metal selected from the group consisting of alkali metals, alkaline earth metals and transition metals; and x represents the stoichiometric valence requirement of the molecule. By stoichiometric valence requirement, applicant means the number of organic moieties having a negative charge required to satisfy the valence requirement of the positive metal atom. For example, if B is sodium x is 1, or if B is Zn x is 2.

The ethylenically unsaturated monomers of the present invention are made by reacting at a temperature range of about 45° C. to about 70° C., an epoxyalkene with sodium metabisulfite in water as a solvent and at a pH in the range of about 3.5 to 5.0, preferably at a pH in the range of about 4.0 to about 5.0, and more preferably at a pH in the range of about 4.5 to 5.0. A particularly preferred temperature range is about 55° C. to about 65° C. Typical epoxyalkenes that can be used as starting materials include epoxybutene (also known as vinyloxirane), 2-methyl epoxy 1-butene, epoxidized isoprene, 3,4-epoxy 1-pentene. More in particular, the starting epoxyalkenes are those corresponding to the formula

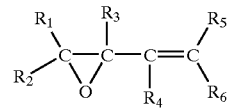

wherein $R_1$, $R_2$, $R_3$, $R_4$, $R_5$, and $R_6$ are independently selected from the group consisting of hydrogen and $C_1$–$C_5$ primary, secondary or tertiary lower alkyl groups.

The reaction stoichiometry for the formation of the monomers of the present invention is illustrated below:

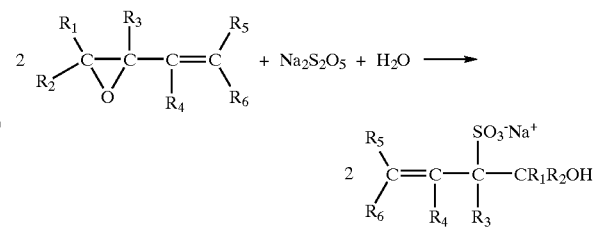

As shown above, the stoichiometry of the reaction is two moles of epoxyalkene and ONE mole of sodium metabisulfite in water to produce two moles of the hydroxy sulfonated alkene derivative.

In a second preferred embodiment, the invention is directed to both homopolymers of compounds of the formula I or II as well as copolymers having at least one repeating unit of compounds of formula I and II with other ethylenically unsaturated monomers. Among such other known polymerizable ethylenically unsaturated compounds are the alkenyl-aromatic compounds, i.e., styrene and o-, m-, and p-vinylstyrene, the derivatives of α,β-ethylenically unsaturated. acids such as the esters, amides, and nitriles of acrylic acid, methacrylic acid, itaconic acid, and maleic acid, unsaturated alcohol esters, unsaturated ketones, unsaturated ethers, and other compounds containing one or more ethylenic linkages, especially those having a single unsaturated group of the formula $H_2C=C-$, capable of addition polymerization. Specific examples of such ethylenically unsaturated compounds are styrene, α-methylstyrene, methylstyrene, ethylstyrene, α, α dimethylstyrene, dimethylstyrene, vinylnaphthalene, hydroxystyrene, methoxystyrene, cyanostyrene, acetylstyrene, monochlorostyrene, dichlorostyrene and other halostyrenes, methyl methacrylate, ethyl acrylate, butyl acrylate, butyl methacrylate, hexyl acrylate, lauryl methacrylate, phenyl acrylate, acrylonitrile, methacrylonitrile, acrylanilide, acrylamide, N-methylolacrylamide, ethyl .alpha.-chloroacrylate, ethyl maleate, polyglycol maleate, vinyl acetate, vinyl propionate, vinyl butyrate, vinyl benzoate, vinyl chloride, vinyl bromide, vinylidene chloride, vinylidene bromide, vinyl methyl ketone, isopropenyl ketone, vinyl ethyl ether, and dienes which generally act as though they have only one point of unsaturation during normal polymerization, such as 1,3-butadiene, isoprene, and the like.

The monomers of formula I and II and their water-soluble salts may be homopolymerized in bulk or in an aqueous solution thereof using a suitable polymerization catalyst or initiator or an initiator system, such as a redox system. The catalyst or initiator may simply be radiation, especially ultra-violet light, or it may be a free radical type of initiator, miscible with the monomer or soluble in the aqueous medium. Examples include hydrogen peroxide, ammonium or an alkali metal (e.g. sodium or potassium) persulfate, t-butyl hydroperoxide, cumene hydroperoxide or azo-bisisobutyronitrile. Such initiators may be used in the customary amounts of about 0.1 to 3% by weight based on total monomer weight. In redox systems, a free radical initiator, such as the type mentioned is used with a reducing agent, such as sodium hydrosulfite, potassium inetabisulfite, or ascorbic acid, in comparable amounts, e.g. 0.1 to 3% based on monomer weight. Any suitable pH may be maintained such as in the range from 3 to 10, an acid, base, and/or buffering agent or agents being included as desired.

Homopolymers and copolymers can also be produced in any other solvent medium, such as an ester, e.g. ethyl acetate, a ketone, e.g., acetone or methyl isobutyl ketone, an ether, e.g. dioxane, and the dimethyl ether of diethylene glycol, or mixtures containing two or more such solvents or containing water and one or more of the organic solvents just mentioned. Alcohols are unsuitable for use as the solvent medium whenever complex ester product mixtures are to be avoided. An initiator or initiator system that is soluble in the medium may be used, such as any of those mentioned above for use in the aqueous systems.

Copolymers of one or more other monomers, such as those previously mentioned, with a monomer of formula I and II can be produced efficiently in an aqueous medium, with and more particularly without the use of an emulsifying agent to aid in the dispersion of any water-insoluble monomer. When an emulsifier is used, it may be used in conventional amount in the range of 0.05 to 6% or more based on the weight of water-insoluble monomer used in the polymerization process. The water-soluble initiator or initiator systems mentioned above may be used in the amounts stated. Generally, the polymers produced have high molecular weight, such as from about one million to ten millions or more. However, a chain transfer agent, such as bromotrichloroethane, methylene chloride, a $(C_2–C_{12})$alkyl mercaptan, e.g. dodecyl mercaptan, or a hydroxyalkyl mercaptan, e.g. β-hydroxyethyl mercaptan, may be used to obtain polymers of lower molecular weights, such as from about 10,000 to any point below that which the system in use normally produces without such an agent, the more of the agent used, the lower the molecular weight for any particular chain transfer agent. The amount of such an agent used may be from about 0.05% to 10% or more based on the total monomer weight.

A suspension polymerization technique of normal type employing a colloid, such as polyacrylic acid or poly(α-vinylpyrrolidinone), may be used to form copolymers containing a large proportion of at least one monomer of formula I and/or II cross-linked by about to 5 to 50% (preferably 15 to 35%) by weight of a diethylenically unsaturated copolymerizable monomer such as divinyl benzene, ethylene glycol dimethacrylate, or diallyl phthalate. Such polymers are obtained in the form of beads or granules which are useful as cation-exchange resins.

The monomers of formula I and II as well as the homopolymers of a monomer of formula I and II herein and copolymers formed largely (at least 55% by weight) of one or more monomers of formula I and II and containing 0% to 45% by weight of other monomers of the types mentioned hereinabove are useful as surfactants, such as wetting agents, as antistatic agents for textiles and other articles formed of hydrophobic materials such as nylon, cellulose esters, and polyesters and as softening agents for textiles, such as cotton and rayon. They are also useful as conductivity aids in paper, such as that used in electrostatic reproduction. They are also useful to stabilize aqueous polymer dispersions and water-base paints against coagulation as a result of freezing and subsequent thawing. They, and especially the polymers, are useful as flocculating agents. To serve these purposes, the amount of the monomer or polymer needed is quite small relative to the magnitude of the system to which or in which they are applied. When a relatively small amount of a monomer of formula I and/or II is incorporated as a polymerized component in water-insoluble polymers used in the coatings industry, the copolymers that are obtained show remarkable improvements in adhesion to various substrates, and especially those of, or carrying a deposit of, a plastic or resinous material.

The polymers contemplated here are the addition polymers of at least one monoethylenically unsaturated monomer having a group of the formula $H_2C=C-$, including a vinyl ester of a $(C_1–C_{18})$alkanoic acid, e.g. vinyl acetate, vinyl versatate, and vinyl dodecanoate; a $(C_1–C_{18})$alkyl ester of acrylic acid or methacrylic acid, such as methyl acrylate, methyl methacrylate, ethyl acrylate, ethyl methacrylate, butyl acrylate, butyl methacrylate, 2-ethylhexyl acrylate or methacrylate; a vinyl-aromatic hydrocarbon, such as styrene and vinyltoluene; acrylonitrile, acrylamide and so forth.

Thus the copolymers containing from as little as 0.1% by weight, based on copolymer weight, up to 2% or 5% by weight of a monomer of formula I and/or II are exceptionally useful for improving the adhesion of coatings of compositions comprising such copolymers when applied to substrates of metal, glass, or plastic carrying a deposit of a vic-epoxy resin primer, an aminoplast resin primer, or primers formed of mixtures of such resin-forming substances, all of which are of commercial types commonly available on the market.

Copolymers of monoethylenically unsaturated compounds containing small amounts of a monomer of formula I and/or II such as from about 0.2% to 5% or even up to 10% are useful to impart antistatic properties to textiles and other materials formed of hydrophobic materials, such as nylon, cellulose esters including cellulose acetate and cellulose acetate butyrate, and polymers such as the condensates of ethylene glycol with terephthalic acid. Preferably, such copolymers are prepared by emulsion polymerization processes so that a latex or aqueous dispersion of the polymer is produced containing anywhere from 20 to 60% by weight of the polymer dispersed herein. In applying the dispersion to the fabric or other material the dispersion may be diluted to bout 15 to 30% solids and applied by spraying, use of a textile pad, or brushing as is most suitable for application to the particular substrate involved. Effective antistatic properties are obtained by the application of an amount from about 0.1 to 14% by weight of the polymer based on the weight of fibers in the case of the textile material whereas effective antistatic property is obtained by the application of such a polymer on a solid article such as a molded plastic article when the polymer is deposited in the form of a thin film of about 1–10 microns thickness.

In a third preferred embodiment, the polymerizable anionic emulsifying agent of the invention is added into an emulsion polymerization system to make emulsion polymerization proceed the same as in a normal nonpolymerizable emulsifying agent. The polymerizable anionic emulsifying agent per se is also copolymerized with other monomers and chemically bonded within a polymer molecule. Then, the residual amount of the emulsifying agent is infinitesimal when the polymerization terminates. Therefore, it is possible to minimize the discharge of environmental pollutants which are discharged together with industrial wastes at the time of separating the polymer from latex through salting-out, filtration and washing.

In order to exhibit the effect of preventing discharge of environmental pollutants most effectively, it is necessary to employ the present polymerizable anionic emulsifying agent according to the following means. That is to say, 93 to 99.5% by weight of α, β-ethylenically unsaturated monomer having solubility of not more than 10% by weight to water at 35° C. and 0 to 2% by weight of α, β-ethylenically unsaturated monomer having a solubility of more than 10% by weight to water at 35° C. must be copolymerized in the presence of 0.5 to 5% by weight of the present polymerizable anionic emulsifying agent in an aqueous medium.

The polymerizable anionic emulsifying agent in the invention has the similar emulsifying function to a conventional anionic emulsifying agent. The emulsifying agent forms micelle in the aqueous medium by which the monomer is solubilized and the resultant polymer particles are protected by chemically bonding so that a stable polymer dispersion is provided.

One of the principal advantages of the hydroxyl and sulfonate substituted alkenes of the present invention is that enviromental pollution due to the drainage can be prevented by the employment of the present polymerizable anionic emulsifying agent under specific conditions. Since the hydroxyl and sulfonate substituted alkenes of the invention adequately copolymerize with α, β-ethylenically unsaturated monomer, the water-soluble copolymerized material being abundant in the emulsifying agent, the emulsifying agent is chemically bonded to the polymer in high quantities. Therefore, the emulsifying agent employed in the polymerization is scarcely discharged into the drainage as an unreacted emulsifying agent, a water-soluble polymeric material or a homopolymer when the polymer is recovered from the polymer dispersion through salting out, filtration and washing.

Another principal advantage of the present invention is that the deterioration of quality of a shaped article prepared therefrom can be prevented. In case of manufacturing shaped articles such as film, fiber, or the like, from the polymer prepared by employing a conventional emulsifying agent, the obtained shaped article is inferior in transparency, heat stability, mechanical property, fastness to light, chemical resistance or water resistance since the employed emulsifying agent remains in the polymer with it being adsorbed even if water washing of the polymer is carried out with large amounts of water. However, according to the present invention, the polymerizable anionic emulsifying agent is chemically bonded within the polymer molecule obtained by the copolymerization since the emulsifying agent can adequately copolymerize with the α, β-ethylenically unsaturated monomer.

In another embodiment of the present invention, particularly for producing the emulsifier-free aqueous polymer emulsion of the present invention is that the amount of use of the monomer represented by the general formula (I) or (II) should be within the range of 0.01 to 30 weight % based on the total monomer mixture to be copolymerized. When the amount of use is less than 0.01 weight %, the chemical stability, the attainment of which is an object of the present invention, cannot be obtained, and on the other hand when it exceeds 30 weight %, the physical properties of the film formed from the emulsion, especially the mechanical strength and water resistance, will seriously lowered, and the film cannot be submitted to practical use. In order to bring the chemical stability of the emulsion and the physical properties of the film produced therefrom within a more preferred range in practical use, it is preferable to maintain the amount of use of the monomer represented by the general formula (I) or (II) within the range of from 0.5 to 10 weight %.

When making acrylic resins copolymerized with the monomers of the present invention, the polymerization reaction may also be done by first partially polymerizing the starting acrylic monomer comprising predominantly methyl methacrylate to give a partial polymerizate (in the form of a syrup) and adding thereto a monomer of formula I or II and other ingredients and then continuing the polymerization reaction.

Among the conventional polymerization methods as mentioned above, bulk polymerization is particularly suitable in view of its easy operation. According to so-called "casting polymerization", the desired antistatic acrylic resin cast plate can easily be prepared.

The casting polymerization is usually carried out as follows. To the starting acrylic monomer, i.e. methyl methacrylate alone, or a monomer comprising predominantly methyl methacrylate, or a partial polymerizate thereof (in the form of a syrup), are added a monomer of formula I or II, and other additives, and the mixture is mixed well to give a uniform solution. The solution pe se or after partially polymerizing into the form of a syrup, is admixed with a radical polymerization initiator to give a casting material. The casting material thus prepared is poured between two reinforced glasses which are set face to face, with a space, the periphery thereof being sealed with a gasket, and then subjected to a polymerization reaction with heating. This method is known as "glass cell casting".

Alternatively, the casting material is continuously poured into the space between two metallic endless belts which are run in one direction at a constant speed, one surface of the metallic belt being planished and the periphery of the belts being sealed with a gasket, and then subjected to a polymerization reaction with heating. This method is called "continuous casting". In the present invention, both the glass cell casting and the continuous casting are effectively used.

The methacrylic resin thus obtained has excellent antistatic properties without deteriorating the natural properties of the methacrylic resin, such as transparency, surface gloss, mechanical properties, weatherability, and processability. Moreover, the excellent antistatic properties are changed neither by washing with water nor rubbing, nor with a lapse of time. Thus, the methacrylic resin obtained by the present invention is practically very useful.

As used in this specification the term emulsifier-free aqueous polymer emulsion means those produced without addition of any low molecular weight emulsifier before, during or after polymerization.

In a further embodiment of the invention, the Applicant has also found a process for preparing acrylic polymers in suspension which utilizes, as a suspending agent, a polymeric product which imparts high stability to the suspension, allows to obtain beads endowed with a regular morphology and free from agglomerates, even operating with water/monomer ratios very close to the unit, reduces the fouling of the polymerization reactors, lowers the concentration of the polymer in emulsion in the waste waters to extremely low values and, in the case of polymethylmethacrylate (PMMA), imparts a high optical purity to the product.

The process for preparing acrylic polymers by aqueous suspension polymerization is conducted in the presence of 0.05–1% by weight, calculated on the suspension, of a stabilizer consisting of a polymer obtained by polymerization of: 60–100% by weight of a salt of a monomer having general formula:

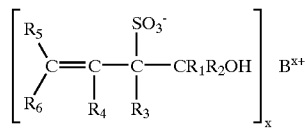

II wherein $R_1$, $R_2$, $R_3$, $R_4$, $R_5$, and $R_6$ are independently selected from the group consisting of hydrogen, and $C_1$–$C_5$ primary, secondary or tertiary lower alkyl group; B is a monovalent or multivalent metal selected from the group consisting of alkali metals, alkaline earth metals and transition metals; and x represents the stoichiometric valence requirement of the molecule; and 0–40% by weight of at least an acrylic monomer. Typically, B represents an alkaline metal or an alkaline-earth metal such as, for example, sodium, potassium, calcium, magnesium, etc.

The new monomers of the present invention are typically copolymerized in aqueous emulsion and the resulting copolymers have improved physical properties such as polymer modulus, solubility, conductivity, and electrostatic properties. Also, the new monomers provide improved water solubility and more in particular they provide self-dispersing properties to the resulting polymers i.e., the resulting polymers don't require additional emulsifiers or dispersing agents. Additionally, the monomers of the instant invention allow the polymer chemist to prepare high solid emulsions because of the stabilizing effect of the monomer containing both hydroxyl and sulfonate moieties.

The resulting copolymers containing varying amounts of the monomer of the present invention also improves the adhesion properties of the resulting polymer to a wide variety of surfaces i.e., organic and inorganic surfaces, they can also be used as thickeners, and they also provide films having improved film strength.

Another use of the resulting copolymers of the invention, is in promoting conductivity and electrostatic charge dissipation. Further uses of the resulting copolymers include wetting of films to facilitate subsequent coating applications such as inks, paints and adhesives.

Other applications wherein the copolymers of the present invention are useful include promotion of high gloss of the resulting films, soil release, stain release, textile wetting applications and antiredeposition in laundering applications.

Applicant's have also found that ampholyte polymers, which comprise: a) acrylamidopropyltrimethyl ammonium chloride or methacrylamidopropyltrimethyl ammonium chloride; b) acrylic acid (AA), methacrylic acid (MM), 4-hydroxy-3-sulfonic acid-1-butene sodium salt and c) optionally, a $C_1$–$C_{22}$ straight or branched alkyl acrylate or methacrylate; are generally useful in cosmetic formulations and provide particularly improved conditioning properties to hair products. Aside from improved conditioning, as measured by combability, substantivity, flyaway and/or feel, these polymers at the same time may improve, but are generally not detrimental to, hair fixative properties such as curl retention.

In a further preferred embodiment of the present invention, an effective amount of an ampholyte polymer described above is added to an anionic surfactant-containing hair or skin care product, preferably a hair care product. Thus, the polymer compositions of the present invention can be used in, inter alia, shampoos, conditioners, rinses, coloring products, bleaching products, setting lotions, blow-drying lotions, restructuring lotions, perms and straightening products.

Aside from hair care uses, skin and nail conditioning products are desired which function to improve properties such as retention of moisture, softening of the skin, attraction of air moisture, retardation of water loss, feel and reduction of skin irritations caused by contact with cosmetic ingredients. Examples of such products include detergents, lotions and soaps.

The present invention is illustrated by the following Examples, but should not be construed to be limited thereto. In the Examples, "part" and "%" are all part by weight or % by weight unless specified otherwise.

EXAMPLE 1

Synthesis of 4-hydroxy-3-sulfonic Acid-1-butene, Sodium Salt

Into a reaction flask equipped with stirring and heating means there is added 1 mol of sodium metabisulfite (190 g) dissolved in 500 g water, followed by addition of 6.4 g of 50% NaOH to a pH of about 4.9. The resulting solution is warmed to about 60° C. and addition of epoxybutene (2.0 moles 140 g) is carried out over an 8 hour period while controlling exotherm and maintaining the temperature at about 60° C. The resultant product is then neutralized with NaOH to a pH of 7.5. The resulting product contains in solution 73% 4-hydroxy-3-sulfonic acid-1-butene, sodium salt; 19% 3-hydroxy-4-sulfonic-1-butene, sodium salt; and 8% 4-hydroxy-3-sulfonic acid-2-butene, sodium salt.

EXAMPLE 2

Synthesis of 4-hydroxy-3-sulfonic Acid 2-methyl-1-butene, Sodium Salt

Into a reaction flask equipped with stirring and heating means there is added 1 mol of sodium metabisulfite (190 g) dissolved in 500 g water, followed by addition of 6.4 g of 50% NaOH to a pH of about 4.9. The resulting solution is warmed to about 60° C. and addition of epoxy 2-methyl 1-butene (2.0 moles 168 g) is carried out over an 8 hour period while controlling exotherm and maintaining the temperature at about 60° C. The resultant product is then neutralized with NaOH to a pH of 7.5. The resulting product contains in solution about 70% 4-hydroxy-3-sulfonic acid 2-methyl-1-butene, sodium salt with the remainder 30% being other isomeric impurities.

EXAMPLE 3

Method of Making Polymer Emulsions

Two hundred and fifty parts of demineralized water and 0.0063 part of ferrous chloride were supplied to a polymerization tank. With the temperature in the tank maintained at 60° C. and under stirring, an aqueous solution composed of 8 parts of 4-hydroxy-3-sulfonic acid-1-butene dissolved in 50 parts of demineralized water, a monomer mixture liquid composed of 52 parts of styrene (St) and 40 parts of butyl acrylate (BuA), 50 parts of a 4% aqueous solution of ammonium persulfate, and 50 parts of a 6.8% aqueous solution of acid sodium sulfite were continuously added dropwise into the polymerization tank from separate supply ports, respectively, to start polymerization. The dropping speed of these monomer and catalyst liquids was adjusted so that the dropping will be completed in 30 minutes. After the termination of the dropping, the polymerization was continued one hour and 30 minutes under the same condition. The aqueous polymer emulsion thus obtained had a solid matter concentration of about 21%, and an average particle diameter of $100\mu$. The emulsion was examined for its chemical stability, and was found to have excellent chemical stability. The mechanical stability was also excellent, and no substantial foaming was observed.

EXAMPLE 4

Preparation of the Homopolymer of 4-hydroxy-3-sulfonic Acid-1-butene, Sodium Salt 630, parts of deionized water are loaded in a reactor and 250 parts of 4-hydroxy-3-sulfonic acid-1-butene, sodium salt are slowly fed, then the pH is adjusted in the range 7–8 with small amounts of soda. After the solution has been flushed with nitrogen to eliminate oxygen and heated at 50° C., the potassium persulphate 0.075 parts and the sodium methabisulphite 0.025 parts are added. Polymerization ends in about 60 minutes. Then it is diluted with 4000 parts of deionized water obtaining a solution containing the homopolymer of 4-hydroxy-3-sulfonic acid-1-butene, sodium salt.

EXAMPLE 5

An aqueous solution (100 parts) containing 40% of the monomer described in Example 1 is charged into a reactor provided with a stirrer. The vessel is dipped in an oil bath and carefully heated with stirring while keeping the inner temperature below 100° C., by which water is distilled off. Into methyl methacrylate partial polymerizate (in the form of syrup) (292 parts), in which polymethyl methacrylate (1.2 part) is dissolved, is uniformly dispersed titanium oxide (1.5 part), and therein are dissolved the material obtained above (6 parts) after distilling the water off and 2,2'-azobisisobutyronitrile (0.3 part). After purging dissolved air under reduced pressure, the mixture is poured into a cell which is formed by two reinforced glasses (distance between the glasses 3 mm) which is spaced with an elastic gasket provided on the periphery thereof, and then subjected to a polymerization reaction at 55° C. for 15 hours, at 80° C. for 3 hours and further at 80° C. for 2 hours to give a methacrylic resin cast plate. having a thickness of 3 mm which has a beautiful, gloss, uniform white color. This cast plate had a surface resistivity of $1.2 \times 10^{11} \omega$, and a half-life of 2 seconds, and the antistatic properties of this product were not deteriotated even by washing with water or with time.

EXAMPLE 6

Methyl methacrylate (98 parts) and ethyl methacrylate (2 parts) are charged into a flask and are dissolved at room temperature. To the mixture is added azobisisobutyronitrile (a polymerization initiator, 0.01 part), and the mixture is stirred at a low speed for about one hour in an oil bath at 70° C. to give a partial polymerizate having a viscosity of 1 poise (in the form of a syrup). In the syrup are dissolved 2 parts of a 40% solution prepared as in Example 1 and titanium oxide (0.7 part), and thereto is added azobisisobutyronitrile (a polymerization initiator, 0.1 part). The mixture is poured into a polymerization cell which comprises two glass plates and a polyvinyl chloride gasket, and then is subjected to a polymerization reaction at 70° C. for 5 hours and then at 110° C. for 1 hour to give a resin plate having a thickness of 3 mm. The resin plate is white and has an excellent surface gloss.

EXAMPLE 7

Ink Manufacture 0.3 G of an oil-soluble dye [TON109 (trade name), manufactured by Mitsui Toatsu Senryo Co., Ltd.] was dissolved in 5 g of styrene to prepare an oil phase component. A total amount of this oil phase component, 8 g of 4-hydroxy-3-sulfonic acid-1-butene, sodium salt and 0.5 g of 2,2-azobis(2-aminopropyl)dihydrochloride were added in 150 g of pure water and the polymerization reaction was conducted with stirring at 80° C. for 5 hours to give a dispersion in which a water-soluble polymer is dissolved and an oil-soluble dye is dispersed (concentration of water-soluble polymer as solid content: 6.7% by weight.

Then, to 23.5 g of this dispersion, 1.5 g of carbon black, 10 g of glycerin as a viscosity adjustor, 10 g of ethanol as an evaporation adjustor and 5 g of diethylamine as a pH adjustor were added, followed by mixing with stirring using a ball mill for 5 hours to give an ink.

Although the present invention has been described with reference to specific details of certain embodiments thereof, it is not intended that such detail should be regarded as limitations upon the scope of the invention, except as and to the extent that they are included in the accompanying claims.

What is being claimed is:

1. A water soluble ethylenically unsaturated monomer selected from the group consisting of formula I and II

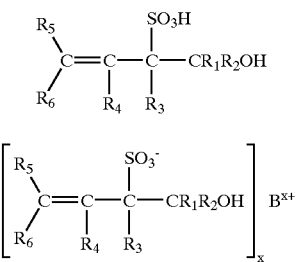

wherein $R_1$, $R_2$, $R_3$, $R_4$, $R_5$, and $R_6$ are independently selected from the group consisting of hydrogen, and $C_1$–$C_5$ primary lower alkyl group; B is a monovalent or multivalent metal selected from the group consisting of alkali metals, alkaline earth metals and transition metals; and x represents the stoichiometric valence requirement of the molecule.

2. The ethylenically unsaturated monomer of claim 1 corresponding to formula I wherein $R_1$, $R_2$, $R_3$, $R_4$, $R_5$, and $R_6$ are all hydrogen.

3. The ethylenically unsaturated monomer of claim 1 corresponding to formula II wherein $R_1$, $R_2$, $R_3$, $R_4$, $R_5$, and $R_6$ are all hydrogen and B is sodium.

4. The ethylenically unsaturated monomer of claim 1 corresponding to formula I wherein $R_4$ is methyl, and $R_1$, $R_2$, $R_3$, $R_5$, and $R_6$ are hydrogen.

5. The ethylenically unsaturated monomer of claim 1 corresponding to formula II wherein $R_4$ is methyl, and $R_1$, $R_2$, $R_3$, $R_5$, and $R_6$ are hydrogen and B is sodium.

* * * * *